US012714549B2

(12) United States Patent
Lamraoui et al.

(10) Patent No.: US 12,714,549 B2
(45) Date of Patent: Aug. 25, 2026

(54) METHOD FOR DRAINING A MEDICAL DEVICE ADAPTED TO BE IMPLANTED

(71) Applicant: UROMEMS, Grenoble (FR)

(72) Inventors: Hamid Lamraoui, Vaulnaveys le Haut (FR); Pierre Mozer, Vincennes (FR); Aurélien Beaugerie, Issy-les-Moulineaux (FR); Riaz Mir, Fontaine (FR); Thierry Ho, Saint Egreve (FR)

(73) Assignee: UROMEMS, Grenoble (FR)

( * ) Notice: Subject to any disclaimer, the term of this patent is extended or adjusted under 35 U.S.C. 154(b) by 1122 days.

(21) Appl. No.: 17/781,224

(22) PCT Filed: Dec. 15, 2020

(86) PCT No.: PCT/FR2020/052446
§ 371 (c)(1),
(2) Date: May 31, 2022

(87) PCT Pub. No.: WO2021/123604
PCT Pub. Date: Jun. 24, 2021

(65) Prior Publication Data
US 2022/0409353 A1 Dec. 29, 2022

(30) Foreign Application Priority Data
Dec. 16, 2019 (FR) ...................................... 1914526

(51) Int. Cl.
*A61F 2/26* (2006.01)
*A61F 2/00* (2006.01)

(52) U.S. Cl.
CPC .......... *A61F 2/0036* (2013.01); *A61F 2/0095* (2013.01); *A61F 2/26* (2013.01)

(58) Field of Classification Search
CPC .................. A61F 2/0095; A61F 2/0004; A61F 2002/30581; A61F 2002/30584
See application file for complete search history.

(56) References Cited

U.S. PATENT DOCUMENTS 4,597,765 A 7/1986 Klatt
4,750,619 A 6/1988 Cohen et al.
(Continued)

FOREIGN PATENT DOCUMENTS

JP S61154664 A 7/1986
WO 2016083428 A1 6/2016

OTHER PUBLICATIONS

PCT Search Report in related PCT Application No. PCT/FR2020/052446, mailed Apr. 9, 2021.
(Continued)

*Primary Examiner* — Christopher D. Prone
(74) *Attorney, Agent, or Firm* — Thomas | Horstemeyer, LLP

(57) ABSTRACT

The invention relates to a method for draining a medical device adapted to be implanted in a human or animal body, said medical device comprising a housing that encloses a fluid reservoir, and a fluid outlet that forms a fluid connection between the reservoir and a volume outside the housing, the method involving: —providing the device in packaging comprising a tank, the housing being held in the tank in a position in which the reservoir is located between the bottom of the tank and the fluid outlet; —filling the tank with a biocompatible fluid such that a zone of the packaging which lies outside the medical device and is in fluid connection with the fluid outlet of the tank is immersed in the fluid; —draining the medical device and filling the reservoir with the biocompatible fluid.

12 Claims, 3 Drawing Sheets

(56) References Cited

U.S. PATENT DOCUMENTS 5,964,261 A * 10/1999 Neuenfeldt .......... A61K 9/0024
206/439
10,350,044 B2 7/2019 Lamraoui

OTHER PUBLICATIONS

French Search Report in related, co-pending French Application No. FR 1914526, mailed Oct. 9, 2020.

* cited by examiner

METHOD FOR DRAINING A MEDICAL DEVICE ADAPTED TO BE IMPLANTED

CROSS REFERENCE TO RELATED APPLICATIONS

This application is the 35 U.S.C. § 371 national stage application of PCT Application No. PCT/FR2020/052446, filed Dec. 15, 2020, which application claims the benefit of French Application No. FR 1914526 filed Dec. 16, 2019, both of which are hereby incorporated by reference herein in their entireties.

TECHNICAL FIELD

The invention relates to a packaging for a medical device adapted to be implanted in a human or animal body comprising a fluid reservoir.

STATE OF THE ART

Various implantable medical devices include a biocompatible fluid reservoir coupled to a fluid circuit. Such a fluid circuit may, for example, enable actuation of an element of the device.

For example, a device for selectively closing an anatomical duct, such as the urethra or bladder neck, may include an occlusive cuff surrounding said anatomical duct and fluidly coupled to a fluid reservoir. A pump is used to transfer fluid from the reservoir to the cuff so as to increase the compression exerted by the cuff on the duct, or from the cuff to the reservoir so as to reduce the compression exerted by the cuff on the duct.

Other applications involving a fluid reservoir in a medical device implanted in a patient's body relate to the inflation of a closing balloon, or the filling of a prosthesis.

In general, the medical device adapted to be implanted is provided to the surgeon empty of any biocompatible fluid, in a packaging with sterile contents. The surgeon therefore has to expel the air and fill the reservoir with biocompatible fluid before implantation in the patient.

This filling operation has to be implemented so as to drain the fluid circuit of the air initially contained. Indeed, any air bubbles are likely to affect the operation of the implantable device and in particular its accuracy.

Another constraint of the filling operation is to maintain sterility of the device.

Manual filling of the device by the surgeon extends the duration of the surgical procedure and induces a risk of contamination of the device, likely to induce infections or complications in the patient.

Pre-filled medical devices exist, but they have many disadvantages, such as for example during the sterilization step, where it has to be ensured that the fluid is also sterilized through the device.

BRIEF DESCRIPTION OF THE INVENTION

A purpose of the invention is therefore to define a method for draining a medical device adapted to be implanted comprising a fluid reservoir which does not require handling of the device.

To this end, a first object of the invention relates to a method for draining a medical device adapted to be implanted in a human or animal body, said medical device comprising a casing enclosing a fluid reservoir and a fluid outlet forming a fluid connection between the reservoir and a volume external to the casing, comprising:

- providing the device in a packaging comprising a tank, the casing being held in the tank in a position in which the reservoir is positioned between the bottom of the tank and the fluid outlet,
- filling the tank with a biocompatible fluid, so that a zone of the packaging external to the medical device which is in fluid connection with the fluid outlet of the tank is immersed in the fluid,
- draining the medical device by filling the reservoir with the biocompatible fluid and discharging the air present in the reservoir to the fluid outlet.

Preferably, the biocompatible fluid may be a liquid.

The method may include a step of checking horizontality of the bottom of the tank.

According to one embodiment, said checking is based on a horizontality indicator of the fluid level in the tank.

According to another embodiment, possibly combined with the previous one, said horizontality checking is performed by means of an accelerometer of the medical device.

Alternatively or additionally to the two preceding embodiments, the tank is immersed in a container filled with a fluid to obtain horizontality of the bottom of the tank.

In some embodiments, draining the medical device is performed by moving a movable wall of the tank to vary a volume of the tank.

Said movement of the movable wall of the reservoir may be performed by an electromechanical actuator arranged in the casing.

In some embodiments, the casing includes a single fluid outlet and a single fluid connection between the reservoir and said fluid outlet.

In some embodiments, the medical device is adapted to control an occlusion of a natural duct of the human or animal body.

In some embodiments, the medical device is selected from the group consisting of an artificial sphincter, an artificial muscle, an electrical stimulator, a gastric band, a neurostimulator and a penile implant.

BRIEF DESCRIPTION OF THE DRAWINGS

Further characteristics and advantages of the invention will be apparent from the following detailed description, with reference to the appended drawings, in which.

DETAILED DESCRIPTION OF EMBODIMENTS

Figure 1:
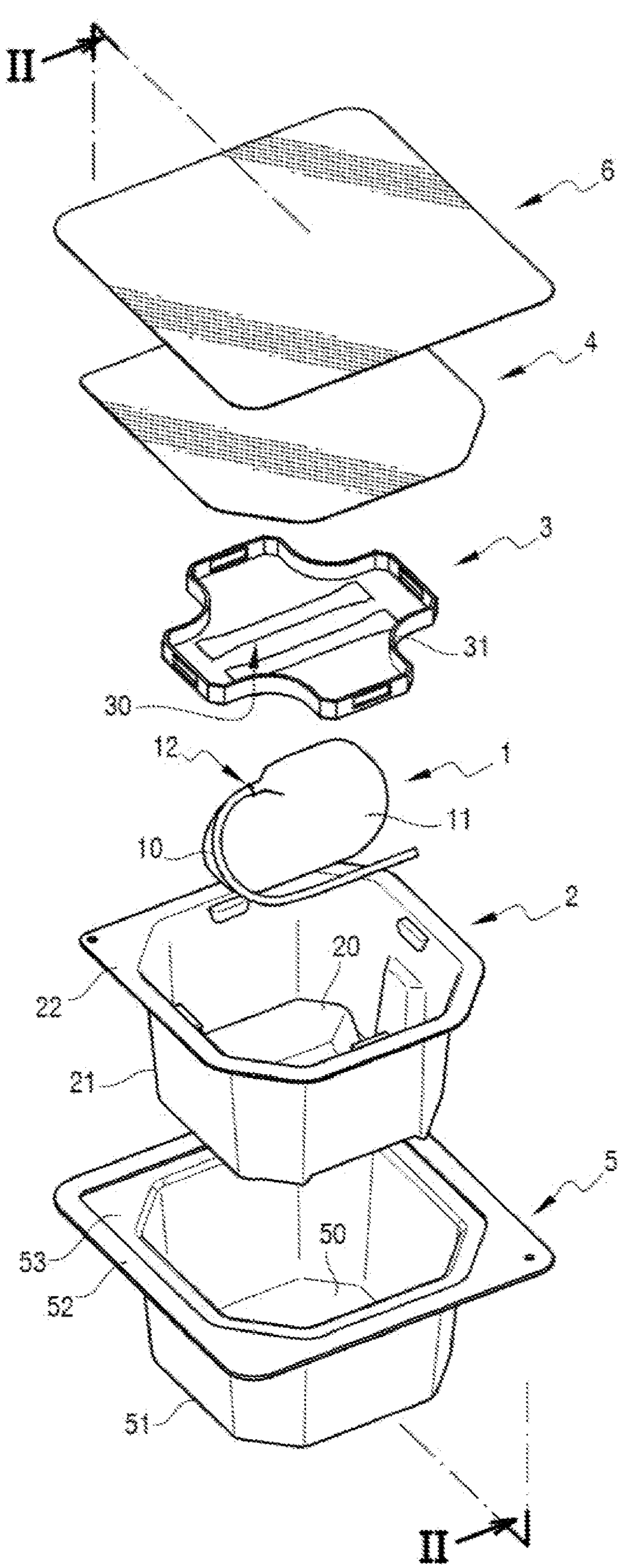
FIG. 1 is an exploded view of a packaging according to one embodiment.

The medical device includes a casing made of a biocompatible material, such as titanium.

The casing contains a reservoir of biocompatible fluid and is provided with a fluid outlet that forms a fluid connection between the reservoir and the environment external to the medical device. Said fluid outlet may especially be connected to a tubing providing a fluid connection with an element external to the casing.

According to one embodiment, the reservoir comprises a movable wall, driven by an actuator, the movement of which makes it possible to vary the volume of the reservoir in a controlled manner. This volume variation allows fluid to be moved from the reservoir to the fluid outlet or from the fluid outlet to the reservoir.

Particularly advantageously, the actuator is an electromechanical actuator, which is controlled by a control unit to move the movable wall by a determined distance. The control unit can be arranged in the casing. The medical device is thus autonomous, in that it does not require action by the practitioner to perform its function.

Furthermore, the device advantageously comprises a single fluid outlet and a single fluid circuit between the reservoir and the fluid outlet.

In some applications, the medical device is an artificial sphincter, for selectively closing an anatomical duct by exerting a compressive force on said duct. In particular, the medical device may be an artificial urinary sphincter.

In such a device, the compression is exerted on the anatomical duct by means of an occlusive cuff connected to the fluid outlet of the casing by a tubing. The electromechanical actuator, by moving the movable wall, allows fluid to be transferred from the reservoir to the cuff or from the cuff to the reservoir, in order to adjust the compression exerted by the cuff.

Examples of such a medical device are described in WO 2016/083428.

Such a device differs from artificial sphincters comprising a pump manually operable by the patient, a pressure regulating balloon, and a cuff, in that the device has controllable autonomous operation, without repetitive manual action by the patient.

In other applications, the medical device may be an artificial muscle, an electrical stimulator, a gastric band, a neurostimulator or a penile implant (non-limiting list).

Between the manufacturing site of the medical device and the operating room in which the medical device is implanted in a patient, the medical device is arranged in a packaging. Said packaging is adapted to maintain medical device sterile by protecting it from external contamination and to protect it from impact. In the packaging, the medical device is empty of biocompatible fluid, filling of the fluid circuit being performed only in the operating room.

As described later, said packaging is further adapted to allow the fluid circuit to be drained without handling of the medical device by a practitioner in the operating room.

The packaging first comprises a tank in which the medical device is held in a so-called vertical position, that is in which the reservoir is positioned between the bottom of the tank and the fluid outlet.

The tank comprises a horizontal bottom, a sidewall, an upper face opposite the bottom in the vertical direction.

The tank includes at least one opening configured to allow filling of the tank with a biocompatible fluid.

The fluid outlet of the medical device is located below said opening, so that when the tank is filled, the entire medical device, including the fluid outlet, is immersed in the fluid.

To ensure that the filling of the tank with biocompatible fluid is sufficient to implement the draining method, the tank can advantageously include a visual liquid level indicator disposed in the top part of the tank. Advantageously, the volume of the tank and the position of the indicator have been chosen and dimensioned to allow filling of the device tank.

Alternatively, the tank can include a cavity in the upper part for receiving an overflow of biocompatible fluid so as to regulate the running over of this fluid and avoid overfilling.

The medical device is held in the vertical position by a first holding element arranged on the bottom, the sidewall and/or the upper face of the tank.

According to one embodiment, said first holding element is in the form of a housing whose dimensions are adapted to receive a part of the casing by exerting a slight clamping action to hold it in the desired position, without damaging it.

Advantageously, said housing is arranged in the bottom of the tank.

According to a preferred exemplary embodiment, the tank is made, for example, by molding or forming a plastic material, and the housing is integrated into the bottom of the tank by molding or forming. The housing may, for example, be in the form of two parallel partitions spaced apart by the width of the casing.

In some embodiments, the medical device may be packaged with a tubing in fluid connection with the fluid outlet. In this case, the tank advantageously comprises a second holding element arranged on the bottom and/or sidewall of the tank to hold a portion of said tubing below the fluid outlet.

Advantageously, said second holding element is in the form of a housing arranged in the bottom of the tank, parallel to the casing housing. This housing may, for example, be in the form of two parallel partitions spaced apart by the diameter of the tubing.

According to one adapted embodiment, represented in the figures, the tank has a parallelepiped shape comprising a four-sided sidewall and a bottom, the face opposite the bottom being open. However, this particular shape is by no means limiting.

Thus, according to other exemplary embodiments not illustrated, the tank may have any other shape, such as a cylindrical shape, for example, with a cylindrical sidewall and a circular bottom.

Particularly advantageously, the bottom of the tank has substantially identical dimensions in two orthogonal directions in a horizontal plane, in order to ensure the stability of the tank, and especially to avoid any tipping of the tank when the medical device is drained.

According to some embodiments not illustrated, the opening of the tank may not be located on the upper face of the tank but on the sidewall of the tank, preferably in an upper portion of said wall so as to be above the fluid outlet of the medical device.

In any case, the tank is dimensioned and the opening is arranged so that, when the bottom of the tank extends in a horizontal plane, the tank can be filled with biocompatible fluid at least to the level of the fluid outlet of the medical device, preferably above said outlet. Thus, upon draining, the entire fluid circuit extending between the tank and the fluid outlet can be filled with biocompatible fluid and drained of the air initially present.

Advantageously, the packaging further comprises a cover removable from the tank so as to at least partially close the opening. The cover is preferably snap fitted onto the sidewall, and retained thereon by friction or snap fitting, for example.

According to a preferred embodiment, the cover is configured to be secured to only a part of the sidewall, the cover having at least one gripping zone remote from the sidewall. For example, the cover may have an outline with a part coinciding with the shape of the opening defined by the sidewall and a part recessed from the sidewall, to form a passage for the practitioner's fingers to facilitate gripping the cover.

Particularly advantageously, the cover has another holding element adapted to hold the medical device in the vertical position. This holding element may be in the form of a housing arranged facing the housing formed in the tank. Thus, the medical device is held in the vertical position in two places, which improves its stability especially during its transport.

Like the tank, the cover can be made by molding or forming a plastic material, and the housing is integrated inside the cover by molding or forming. The housing may, for example, be in the form of two parallel partitions spaced apart by the width of the casing.

In some embodiments, the packaging includes a tub for containing the tank. The tub provides additional protection for the medical device against impact. Advantageously, the tub also forms a sterile enclosure for the tank, thereby improving protection of the medical device from external contaminants. Preferably, during the implantation procedure, the tub can be handled and opened outside the sterile field of the operating room so that the tank can be extracted from the tub and passed into the sterile field. The tank is then opened and handled by the practitioner in the sterile field. Furthermore, as explained below, the tub can be used in the draining method by being filled with biocompatible fluid.

The medical device packing method can be implemented as follows, with the packaging illustrated in FIG. 1.

The assembled medical device 1 is placed in the tank 2. To this end, the medical device is engaged in the holding element(s) provided in the tank to hold said device with the fluid outlet above the reservoir. When the fluid outlet is connected to a tubing, said tubing is preferably also engaged in the holding element(s) provided in the tank to hold said tubing at the bottom of the tank.

Figure 2:
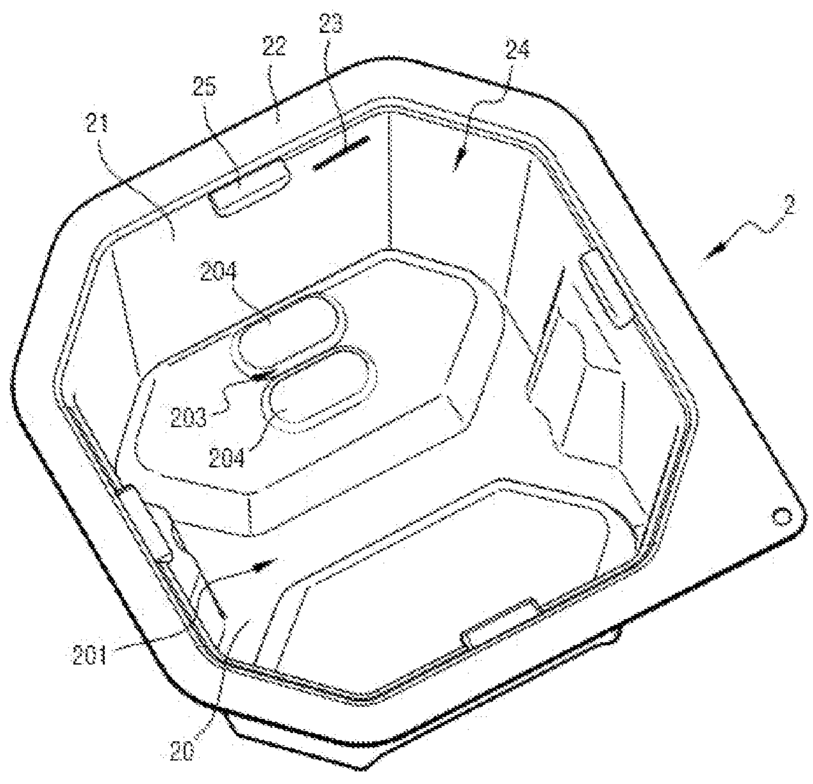
FIG. 2 is a perspective view of the tank.

With reference to FIG. 2, the tank 2 comprises a bottom 20 and a sidewall 21 extending substantially vertically from the bottom 20. On the side opposite the bottom 20, the sidewall 21 has an edge 22 that extends outwardly in a horizontal plane. Said edge 22 defines an upper face of the tank provided with an opening 24.

Figure 3:
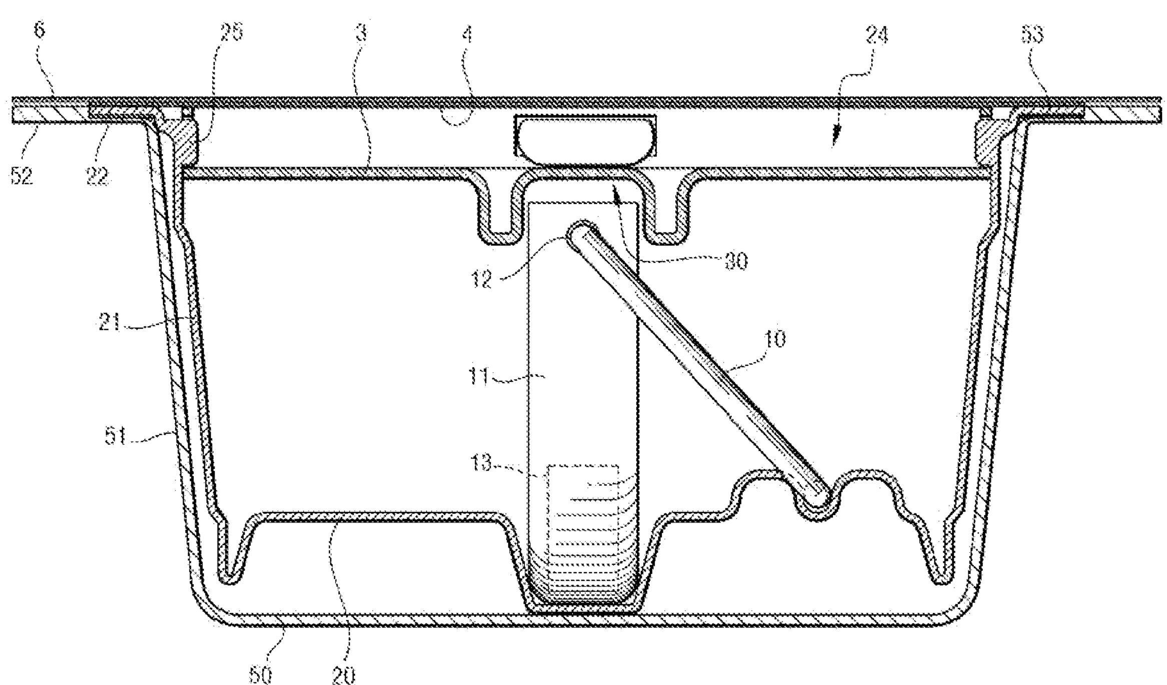
FIG. 3 is a cross-section view of the assembled packaging of FIG. 1.

The medical device 1 includes a casing 11 in which a biocompatible fluid reservoir 13 is arranged (depicted in dotted lines in FIG. 3). The medical device 1 further comprises a fluid outlet 12 which is connected to the casing 11 and in fluid connection with the reservoir 13. The fluid outlet 12 provides a fluid connection between the reservoir and the outside of the casing. The fluid outlet 12 is connected to a tubing 10, which is to be connected, during implantation, to the occlusive cuff.

The height of the sidewall 21 is greater than the height of the medical device in its vertical packing position. Thus, when the medical device 1 is arranged in the tank 2, as illustrated in FIG. 3, the medical device is fully contained within the tank 2. The fluid outlet 12 is arranged below the opening 24, so that it can be covered with fluid when the tank is filled. The reservoir 13 is arranged below the fluid outlet 12 when the medial device is disposed in the tank.

The bottom 20 has a substantially square shape to ensure stability of the tank.

The bottom 20 of the tank 2 includes a housing 201 adapted to hold the medical device in a vertical position. The housing 201 is defined as a cavity formed in the bottom 20, parallel to one of the sides, and extends substantially between the middle of one side and the middle of the opposite side of the bottom 20. The location of the housing is in a central region of the bottom to ensure stability of the tank-medical device assembly when the medical device is arranged in the housing and the tank is filled with biocompatible fluid. The width of said housing is substantially equal to the width of the medical device, to allow the medical device to be inserted and held in said housing. The depth of the housing is chosen so as to avoid any topple of the casing 11; a depth of 5 to 15 mm is adapted to this function.

Particularly advantageously, the housing 201 is provided with two pairs of rounded protrusions (not illustrated), wherein the protrusions of each pair are arranged facing each other in the width direction of the housing 201. Each pair of protrusions locally restricts the width of the housing 201 and thereby exerts a slight clamping action on the medical device to hold it in position.

The bottom 20 of the tank further includes a housing 203 for the tubing 10 of the medical device. The width of said housing is substantially equal to the diameter of the tubing. Said housing is in the form of two parallel studs 204 raised with respect to the bottom 20. Advantageously, as for the housing 201, the studs have a pair of rounded protrusions (not illustrated) facing each other in the width direction of the housing 203. Said pair of protrusions locally restricts the width of the housing 203 and thus exerts a slight clamping action on the tubing. Advantageously, the housing 203 is parallel to the housing 201.

Alternatively, the housing 201 could be defined by one or more pairs of studs facing each other, raised with respect to the bottom of the tank. As for the housing 203, it could be defined as a cavity in the bottom of the tank. Any other shape adapted to hold the medical device in a vertical position could be used.

The cover 3 is placed on the tank 2. The medical device is then engaged in the holding element(s) provided in the cover to hold said device with the fluid outlet above the tank.

For example, the cover may include, facing the housing 201, a housing 30 formed in the cover. The housing 30 may be defined by two raised studs with respect to the inner surface of the cover, or as a hollow formed in the inner surface of the cover. The width of the housing 30 is substantially equal to the width of the upper part of the medical device 1 in the vertical position.

Advantageously, the cover 3 is substantially cross-shaped. As a result, the cover only closes a part of the upper opening of the tank 2, and leaves openings at the corners of the tank adapted for gripping the cover at gripping zones 31 by a practitioner.

The respective shapes and dimensions of the sidewall 21 and the edge of the cover 3 are chosen to allow the cover to be snap fitted into the tank. In particular, the sidewall 21 may comprise, in its upper part, a rim 25 adapted to retain a respective edge of the cover 3.

A first sheet 4 permeable to a sterilizing gas, for example an inner seal made of Tyvek™, is then sealed to the upper edge 22 of the tank.

The tank 2 is then placed in the tub 5.

The tub 5 has a similar shape to the tank 2 but larger dimensions. Preferably, the tub 5 is of sufficient size to fully receive the tank 2 while minimizing the free space between the tank 2 and the tub 5, in order to minimize the overall size of the packaging.

The tub 5 has a substantially planar bottom 50 and a sidewall that extends substantially vertically from the bottom 50. On the side opposite the bottom 50, the sidewall 51 has an edge 52 that extends outwardly in a horizontal plane. Said edge 52 defines an upper face of the tub provided with a central opening.

Advantageously, the tub 5 has an inner rim 53 providing a support for the edge 22 of the tank 2.

Like the bottom 20 of the tank, the bottom 50 of the tub 5 is substantially square to ensure good stability of the tub.

A second sheet 6 permeable to a sterilizing gas, such as an inner seal made of Tyvek™, is then sealed to the upper edge 52 of the tub 5.

The thus sealed packaging is sterilized by any adapted means, and then packaged in a box (not illustrated) which constitutes the outer envelope in which the medical device is delivered to a practitioner for implantation in a patient.

For this implantation, the practitioner takes the packaging out of the box, removes the second sealing sheet, takes the tank out and then removes the first sealing sheet.

Figure 4:
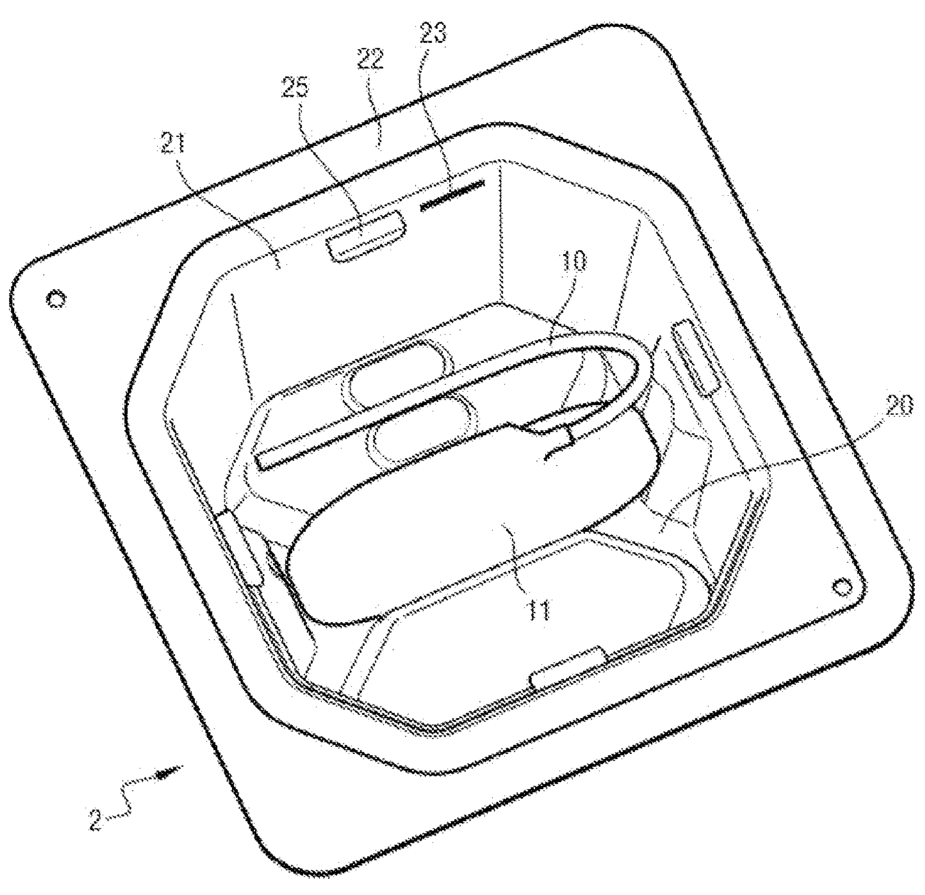
FIG. 4 is a perspective view of the medical device in its packaging.
Figure 5:
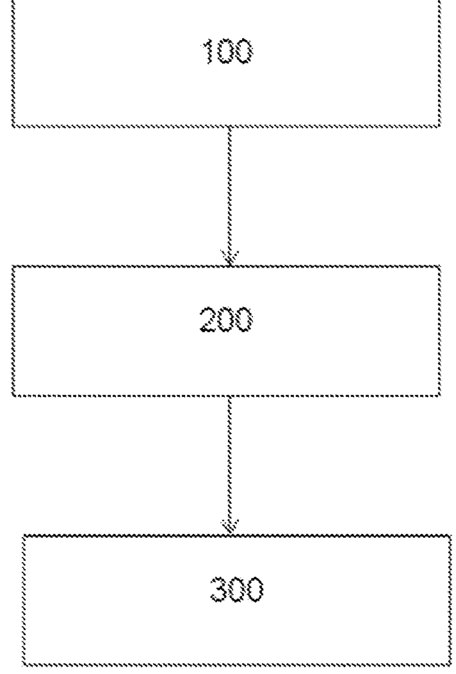
FIG. 5 is a block diagram of a draining method according to one embodiment.

Generally speaking, the method for draining the medical device includes the following steps, the sequence of which is illustrated in FIG. 5:

- in a step 100, the practitioner has the device arranged in the tank, with the casing held in the tank in the vertical position in which it was packaged, as illustrated in FIG. 4; the reservoir is thus positioned between the bottom of the tank and the fluid outlet,
- in a step 200, the practitioner fills the tank with a biocompatible fluid, so that a zone of the packaging external to the medical device that is in fluid connection with the fluid outlet of the tank is immersed in the fluid,
- in a step 300, the draining of the medical device is performed, allowing the filling of the tank with the biocompatible fluid and the extraction of any air initially present in the fluid circuit.

These various steps are described in more detail below.

According to one embodiment, the practitioner takes the tank out of the tub in order to fill it with biocompatible fluid.

To perform this filling and draining, the practitioner has to ensure that the bottom of the tank is horizontal.

Horizontality of the bottom of the tank can be ensured by placing the bottom of the tank on a planar, horizontal surface, such as a table.

This horizontality can be confirmed by means of a suitable indicator. For example, such a horizontality indicator may be an indicator of the horizontality of a water level in the tank. Such an indicator may, for example, be in the form of one or more segments formed in the tank, for example directly by molding or even by printing, and placed in the upper part of the tank, parallel to the bottom. Such an indicator can also serve as a filling indicator for the practitioner, indicating to him or her how high in the tank the biocompatible fluid should be poured in order to allow for effective draining. FIG. 2 illustrates an embodiment of such a horizontality indicator in the form of a hollow or raised interior line 23 extending in a horizontal plane inside the sidewall 21. Preferably, said interior line 23 extends on several sides of the sidewall 21, either continuously or discontinuously.

An indication of the horizontality of the bottom of the tank may also be provided by the medical device itself. Indeed, the device generally includes an accelerometer arranged in the casing, which can be used, when the medical device is implanted, to determine a posture or activity of the patient. Since the casing is integral with the bottom of the tank with a determined orientation relative to it (usually perpendicular), the accelerometer can provide an indication of the inclination of the bottom of the tank.

Alternatively or additionally, this horizontality can be ensured by placing the tank in a container filled with a fluid. In this case, the tank is dimensioned so that when it contains the medical device in the position intended for draining, it floats in the container while holding the fluid outlet of the medical device above the tank.

The tub in which the tank is arranged in the packaging may be used as a container to this end.

The practitioner then fills the tank with biocompatible fluid that is intended for the operation of the medical device. Said fluid may be, for example, saline.

The practitioner then activates the actuator of the medical device to expel air present in the fluid circuit extending between the reservoir and the fluid outlet and into the tubing, if any, and to fill said fluid circuit and tubing with the biocompatible fluid. The actuator can be activated several times, for example three times, causing a movable wall of the reservoir to move to vary a volume of the reservoir and thus exert a pumping action, until the fluid circuit is completely drained (no air bubbles escaping from the fluid outlet).

This activation of the actuator does not require handling of the medical device itself. Indeed, the medical device includes wireless communication means with an outer remote control, which makes it possible to parameterize the device and to send it activation or deactivation orders.

Once the draining is completed, the practitioner can close the fluid outlet or the end of the tubing if any, and take the medical device out of the tank for the implantation operation.

Thus, prior to implantation, the practitioner has not touched the medical device, thus avoiding or at least minimizing the risk of contamination of the device.

In addition, the practitioner's intervention is not required during the draining process. Indeed, once the draining has been initiated, the device's actuator draws in biocompatible fluid and expels air. This allows the practitioner to focus on other tasks, such as implantation preparation. Surgical time can thus be significantly reduced.

Finally, the fact that the draining process is automatic increases the reliability of the method.

It is understood that the embodiments described above are particular and non-limiting examples and that various modifications can be made without departing from the invention

The invention claimed is:

1. A method for draining a medical device adapted to be implanted in a human or animal body, the medical device comprising a casing enclosing a fluid reservoir and a fluid outlet forming a fluid connection between the reservoir and a volume external to the casing, comprising:

- providing the device in a packaging comprising a tank, the casing being held in the tank in a position in which the reservoir is positioned between the bottom of the tank and the fluid outlet, such that the fluid outlet is arranged above the reservoir,
- filling the tank with a biocompatible fluid, so that a zone of the packaging external to the medical device which is in fluid connection with the fluid outlet of the reservoir is immersed in the fluid,
- draining the reservoir of the medical device of air by filling the reservoir with the biocompatible fluid and discharging the air present in the reservoir to the fluid outlet.

2. The method according to claim 1, comprising a step of checking horizontality of the bottom of the tank.

3. The method according to claim 2, wherein said checking is based on a horizontality indicator of the fluid level in the tank.

4. The method according to claim 2, wherein said checking of horizontality is performed by means of an accelerometer of the medical device.

5. The method according to claim 2, wherein the tank is immersed in a container filled with a fluid to obtain horizontality of the bottom of the tank.

6. The method according to claim 1, wherein the step of draining the medical device is performed by moving a movable wall of the reservoir to vary a volume of the reservoir.

7. The method according to claim 6, wherein said movement of the movable wall of the reservoir is performed by an electromechanical actuator arranged in the casing.

8. The method according to claim 1, wherein the casing comprises a single fluid outlet and a single fluid connection between the reservoir and said fluid outlet.

9. The method according to claim 1, wherein the medical device is adapted to control an occlusion of a natural duct of the human or animal body.

10. The method according to claim 1, wherein the medical device is selected from the group consisting of an artificial sphincter, an artificial muscle, an electrical stimulator, a gastric band, a neurostimulator, and a penile implant.

11. A method for draining a medical device adapted to be implanted in a human or animal body, the medical device comprising a casing enclosing a fluid reservoir and a fluid outlet forming a fluid connection between the reservoir and a volume external to the casing, comprising:

providing the device in a packaging comprising a tank, the casing being held in the tank in a position in which the reservoir is positioned between the bottom of the tank and the fluid outlet, filling the tank with a biocompatible fluid, so that a zone of the packaging external to the medical device which is in fluid connection with the fluid outlet of the reservoir is immersed in the fluid, draining the reservoir of the medical device of air by filling the reservoir with the biocompatible fluid and discharging the air present in the reservoir to the fluid outlet, wherein the step of draining the medical device is performed by moving a movable wall of the reservoir to vary a volume of the reservoir, wherein said movement of the movable wall of the reservoir is performed by an electromechanical actuator arranged in the casing.

12. A method for draining a medical device adapted to be implanted in a human or animal body, the medical device comprising a casing enclosing a fluid reservoir and a fluid outlet forming a fluid connection between the reservoir and a volume external to the casing, comprising:

providing the device in a packaging comprising a tank, the casing being held in the tank in a position in which the reservoir is positioned between the bottom of the tank and the fluid outlet, filling the tank with a biocompatible fluid, so that a zone of the packaging external to the medical device which is in fluid connection with the fluid outlet of the reservoir is immersed in the fluid, draining the reservoir of the medical device of air by filling the reservoir with the biocompatible fluid and discharging the air present in the reservoir to the fluid outlet, wherein the medical device is selected from the group consisting of an artificial sphincter, an artificial muscle, an electrical stimulator, a gastric band, a neurostimulator, and a penile implant.

* * * * *